United States Patent [19]

Resh

[11] Patent Number: 4,691,068

[45] Date of Patent: Sep. 1, 1987

[54] PROCESS FOR PRODUCTION OF ALKYL AROMATICS

[75] Inventor: Kyle W. Resh, Baltimore, Md.

[73] Assignee: Vista Chemical Company, Houston, Tex.

[21] Appl. No.: 893,047

[22] Filed: Aug. 1, 1986

[51] Int. Cl.⁴ .............................................. C07C 1/00
[52] U.S. Cl. .................................. 585/323; 585/455; 585/456
[58] Field of Search .................... 585/323, 455, 456

[56] References Cited

U.S. PATENT DOCUMENTS 3,428,701  2/1969  Ward .................................. 585/323
3,433,846  3/1969  Adams et al. ....................... 585/456

Primary Examiner—Curtis R. Davis
Attorney, Agent, or Firm—Browning, Bushman, Zamecki & Anderson

[57] ABSTRACT

An improved process for producing a mono alkyl aromatic by reacting a mono nuclear aromatic compound and an alkylating agent under alkylation conditions to produce the reaction product comprising unreacted mono nuclear aromatic compound, alkane, mono alkyl aromatic, dialkyl aromatic and by-products, treating the reaction product to remove unreacted mono nuclear aromatic compound, free paraffin, and produce a crude product stream containing mono alkyl aromatic, dialkyl aromatic and by-products, separating the majority of the mono alkyl aromatic from the crude product stream to produce a higher boiling fraction containing a minor amount of mono alkyl aromatic, dialkyl aromatic and by-products, and separating the higher boiling fraction into a recycle stream containing mono alkyl aromatic and a by-product stream substantially free of mono alkyl aromatic, and introducing the recycle stream into the alkylation reaction.

8 Claims, 2 Drawing Figures 4,691,068

PROCESS FOR PRODUCTION OF ALKYL AROMATICS

BACKGROUND OF THE INVENTION

1. Field of the Invention

The present invention relates to a process for the production of alkyl aromatics such as alkyl benzene and, more specifically, to an improved method for recovering alkyl aromatics from an alkylation reaction.

2. Description of the Prior Art

The alkylation of aromatic hydrocarbons to produce alkyl aromatic hydrocarbons is well known. Aromatic hydrocarbons can be alkylated by suitable reaction with alkylating agents such as alkenes, halo alkanes, etc., the reaction normally being carried out in the presence of acidic catalysts, such as aluminum chloride, hydrogen fluoride or the like.

The alkyl aromatic compounds produced find widespread uses in many industrial applications. In particular, alkyl aromatic compounds, such as alkyl benzenes, wherein the alkyl group has a chain length of from about 9 to about 14 carbon atoms are particularly useful in producing detergents. Such alkyl benzenes are sulfonated using oleum or sulfur trioxide to produce an alkyl benzene sulfonate, a widely used detergent.

One of the most critical quality parameters for an alkyl benzene sulfonate detergent is the color characteristic. The detergent manufacturing industry generally requires that the alkyl aromatic be a water white product and which upon sulfonation with $SO_3$ or oleum yields light colored sulfonate salts. It is generally believed that alkyl benzenes which are off spec in producing unacceptable dark sulfonate salts contain polynuclear aromatic by-products which, when sulfonated, are yellow to black in color and produce very dark colored sulfonates. It is also known that the sulfonate color precursors, such as naphthalene and anthracene type compounds, have boiling points ranging throughout the alkyl aromatic boiling range, making complete separation by distillation virtually impossible. Accordingly, to meet the essentially pure, water white color, it is common to purge part of the alkyl aromatic fraction from the system, i.e. the tail end or higher boiling point of the mono alkyl aromatic product leaves the process to be sold as a lower value by-product or used for fuel, in an attempt to purge the color precursors from the product. This results in only 97.5 to about 98.5% of the available mono alkyl aromatic in the reaction product being recovered. Even with this expedient, which results in loss of the valuable product mono alkyl aromatic, in order to meet the minimum purity standards required by the detergent manufacturing industry, the recovered mono alkyl aromatic must be further refined with a sulfuric acid wash and contacted with a suitable, basic absorbent such as an Attapulgus clay.

SUMMARY OF THE INVENTION

It is therefore an object of the present invention to provide an improved process for the production and recovery of mono alkyl aromatic compounds.

Yet another object of the present invention is to provide an improved process for producing mono alkyl aromatic compounds which results in a minimum loss of mono alkyl aromatic compounds as a by-product.

Still a further object of the present invention is to provide an improved process for producing mono alkyl aromatic compounds which requires minimal sulfuric acid and clay treatment to remove color causing impurities.

The above and other objects of the present invention will become apparent from the drawings, the description given herein and the appended claims.

The present invention constitutes an improvement on the existing process for producing mono alkyl aromatic in which an aromatic compound, e.g. benzene, and an alkylating agent, e.g. a halo paraffin, is reacted under suitable alkylation reaction conditions e.g. with a Friedel-Crafts catalyst, to produce a reaction mixture containing mono alkyl aromatics, dialkyl aromatics, unreacted benzene, free alkane and higher boiling by-products, the reaction product being treated to neutralize any excess acid. The unreacted aromatic and free alkane are removed from the reaction product to produce a crude product stream containing mono alkyl aromatic, dialkyl aromatic and heavier boiling by-products, the crude product stream being treated, as by distillation, to remove the bulk of the mono alkyl aromatic and produce a heavy boiling fraction containing a minor amount of mono alkyl aromatic, dialkyl aromatic and heavier boiling by-products. The improvement comprises separating substantially all of the mono alkyl benzene from the heavy boiling fraction to produce a recycle stream and returning the recycle stream to the alkylation reaction.

DESCRIPTION OF THE PREFERRED EMBODIMENTS

While the present invention is applicable to any type of alkylation reaction wherein an alkylating agent, such as an halo alkane or an olefin is reacted with a mono nuclear aromatic compound to produce a mono alkyl aromatic, it will be described with particular reference to a Friedel-Crafts alkylation procedure to produce mono alkyl benzenes.

Figure 1:
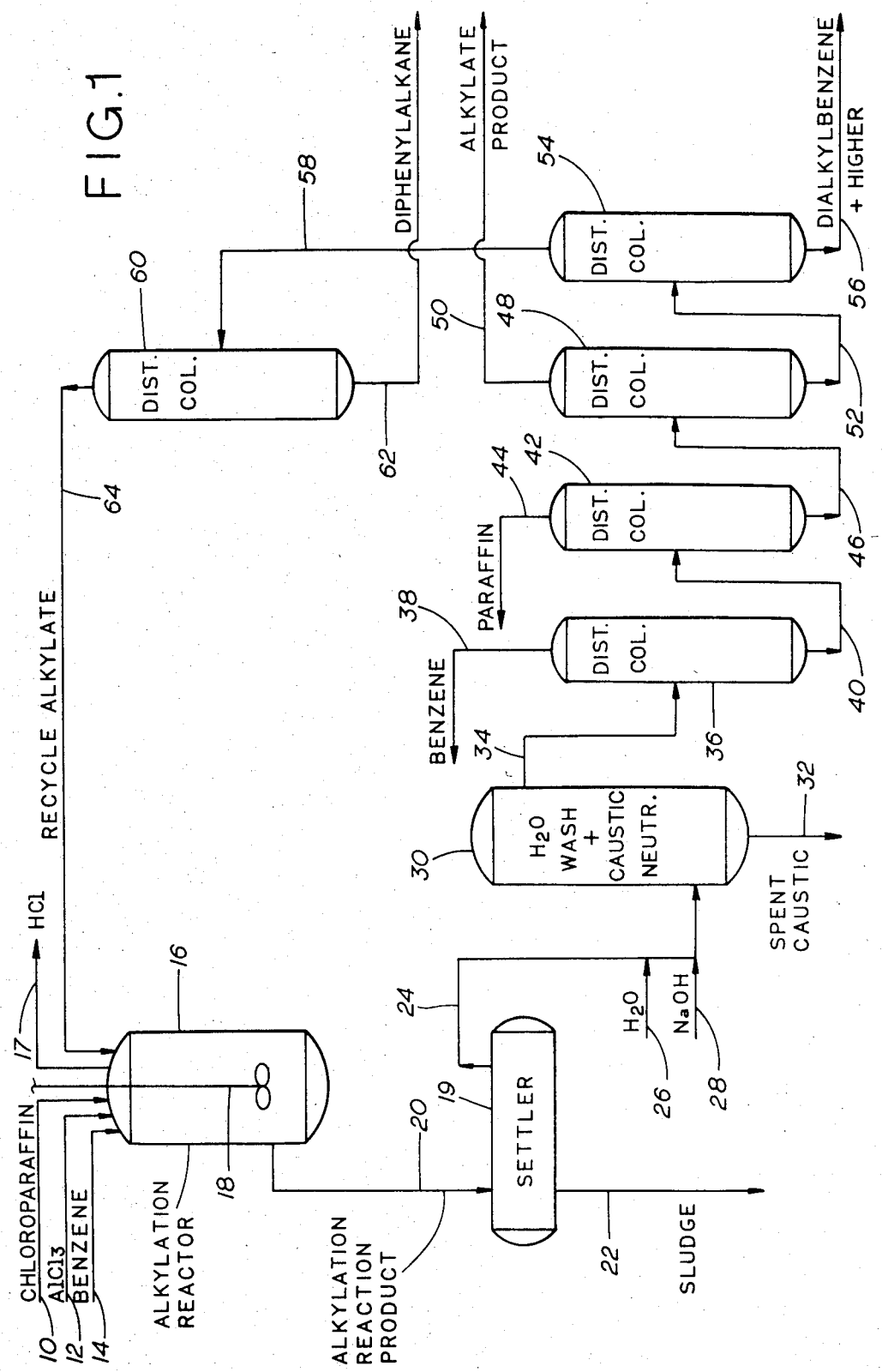
FIG. 1 is a schematic flow diagram of the process of the present invention.

Referring then to FIG. 1, a chloro paraffin in admixture with paraffin via line 10, aluminum chloride via line 12, and benzene via line 14 are introduced into a suitable alkylation reactor 16 which, as shown, is equipped with an agitator 18, conditions in reactor 16 being those generally used by those skilled in the art familiar with Friedel-Crafts alkylation processes.

The alkylation reaction product from reactor 16 contains mono alkyl benzene, dialkyl benzene, unreacted benzene, free paraffins, by-products and catalyst residues and is removed from reactor 16 via line 20, HCl being vented via line 17. The reaction product in line 20 is introduced into settler 19. Sludge and other solid material, primarily by-products from the aluminum chloride catalyst, are removed from settler 19 via line 22. The sludge-free liquid is removed from settler 19 via line 24 and is admixed with water via line 26 and sodium hydroxide or some other suitable neutralization agent via line 28. The mixture enters wash and neutralizer vessel 30 where the excess HCl and other acidic materials are neutralized with the caustic, a water layer containing the spent caustic being removed from vessel 30 via line 32. The neutralized, dewatered reaction product is removed from vessel 30 via line 34 and introduced into distillation column 36 wherein the unreacted benzene is removed as an overhead fraction via line 38, the benzene being recycled for use in subsequent alkylation reactions, the benzene-free reaction product being removed from distillation column 36 via line 40 and being introduced into distillation column 42. In distillation column 42, the paraffins or alkanes initially present with the chloro alkanes are removed as an overhead fraction via line 44, while the reaction produce, now substantially free of paraffins and benzene, is removed from distillation column 42 via line 46 and introduced into distillation column 48. In distillation column 48, the desired product, mono alkyl benzene, is removed as an overhead fraction via line 50 and sent for further processing. A higher boiling, bottom fraction containing a minor amount of mono alkyl aromatic, dialkyl aromatics and heavier by-products is removed from distillation column 48 via line 52 and introduced into distillation column 54 where a bottoms or heavier boiling fraction containing primarily dialkyl benzenes and other, higher boiling by-products, but being substantially free of mono alkyl benzene, is removed via line 56 while a lighter or overhead fraction containing mono alkyl aromatic and some diaryl alkanes, e.g. diphenyl alkane, is removed via line 58 and introduced into distillation column 60. In distillation column 60, the diaryl alkanes, substantially free of mono alkyl aromatics, are removed as a bottom fraction via line 62 while an overhead stream containing mono alkyl aromatics and trace quantities of polynuclear aromatics, e.g. anthracene, naphthalene, are removed as an overhead fraction via line 64 and recycled as a feed to reactor 16.

It will be understood that in the conventional, prior art process, column 60 could be dispensed with, i.e. the diphenylalkane and mono alkyl benzene in line 58 would be removed as lower value products or burned as fuel.

In the process described above, it will be apparent that virtually none of the desired product, i.e. the mono alkyl aromatic, leaves the process in any of the lower value streams, i.e. the streams in lines 56 or 62. Rather, it remains in the loop for recovery as the process continues. In addition, the trace quantities of the polynuclear impurities, which are believed to be the color precursors, are preferentially alkylated to bottoms type products in the alkylation reactor. The alkylated polynuclears are subsequently purged from the system in one of the lower value streams. Thus, the process permits the recovery of virtually all of the mono alkyl aromatic without significant loss and without a build-up of the sulfonate color precursors.

Figure 2:
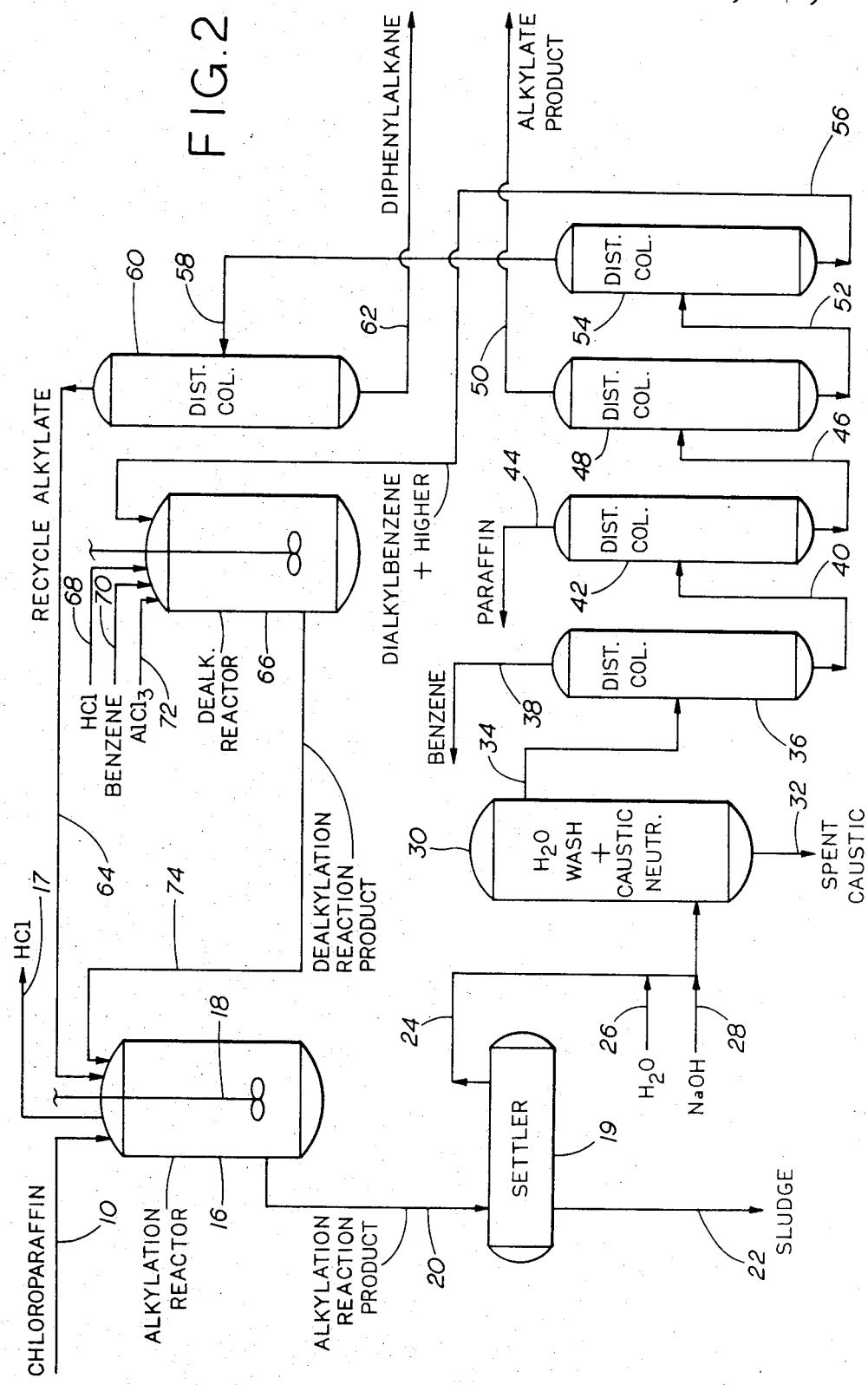
FIG. 2 is a schematic flow diagram showing a variation of the process of the present invention.

Turning now to FIG. 2, there is shown a modified version of the process of FIG. 1. The process shown in FIG. 2 differs from that shown in FIG. 1 only in that at least a portion of the higher boiling stream removed from column 54 via line 56 and containing dialkyl benzene and higher boiling compounds, instead of being removed as a lower value product, is introduced via line 56 into a dealkylation reactor 66 along with hydrogen chloride via line 68, benzene via line 70 and aluminum chloride via line 72. In reactor 66, there is generally a large excess of benzene. This results in an alkyl group transfer giving dealkylation product and mono alkyl aromatic. The dealkylation reaction product is removed from reactor 66 via line 74 and introduced into reactor 16.

In the scheme shown in FIG. 2, it will be apparent that in addition to recovering all of the mono alkyl aromatic initially produced in reactor 16, the di and poly alkyl aromatics produced are dealkylated to produce additional mono alkyl aromatic product, all of this being accomplished without a build-up of the sulfonate color precursors in the process loop.

The process of the present invention is applicable to any alkylation reaction wherein a mono nuclear aromatic compound is reacted with an alkylating agent in a condensation-type reaction to produce an alkyl aromatic hydrocarbon. Virtually any mono nuclear aromatic hydrocarbon can be employed in the alkylation reaction of the present invention, non-limiting examples of which include benzene, toluene, xylene, cumene, etc. Particularly preferred as an aromatic hydrocarbon is benzene. Typical alkylation reactions with which the present invention can be employed include condensation of alkenes with aromatic hydrocarbons such as, for example, the production of ethyl benzene by the reaction of ethylene and benzene (1) in the presence of an acidic catalyst such as $AlCl_3$-HCl or $HF$-$BF_3$ or (2) in the presence of a catalyst such as silica-alumina at elevated pressures. Sulfuric acid and hydrofluoric acid are also effective catalysts in the condensation of alkenes with aromatic hydrocarbons, particularly alkenes having a greater carbon number than ethylene. The process of the present invention is particularly applicable to Friedel-Crafts alkylation procedures in which an aromatic hydrocarbon such as benzene is reacted with an alkylating agent comprising an alkyl halide in the presence of a Friedel-Crafts catalyst such as aluminum chloride, aluminum bromide, boron fluoride, stannic chloride, ferric chloride and certain other metal halides. Alkyl halides employed are preferably alkyl chlorides although other halides can be employed. In addition to use of alkanes and alkyl halides as alkylating agents, alcohols can also be used as alkylating agents as well as small ring cyclo alkanes such as methyl cyclopropane, such alkylating agents being reacted with the aromatic hydrocarbon in the presence of acidic catalysts such as sulfuric acid, hydrogen fluoride, etc.

While the alkylating agent, e.g. the alkene or alkyl halide, can be of any chain length, preferably, the alkylating agent is an alkyl halide and, more preferably, an alkyl chloride or olefin having from 8 to 17 carbon atoms and more particularly from 9 to 14 carbon atoms. The alkyl aromatics having from 9–14 carbon atoms find particular utility in the production of detergent type alkylates. In a typical alkylation reaction according to the present invention utilizing an alkyl halide such as an alkyl chloride, there is generally used a chloro paraffin having from 9 to 14 carbon atoms, about 90% of the chloro paraffins being secondary chloro paraffins, the remaining 10% being primary chloro paraffins.

The relative amounts of the aromatic hydrocarbon, the alkylating agent and catalyst in such alkylating procedures are well known to those skilled in the art and need not be detailed here. Generally speaking, the reaction is carried out in an excess of the aromatic hydrocarbon which serves as a solvent for the reaction. Depending upon the particular type of catalyst employed and the alkylating agent used, the alkylation reaction can be carried out at a wide variety of temperatures and pressures. In the case of the alkylation of the aromatic hydrocarbon and condensation with an alkane and when using an $AlCl_3$-HCl catalyst, the reaction s carried out at moderate temperatures (150°–180° F.) whereas when a silica-alumina catalyst is used in such a reaction, the process is generally conducted at elevated pressures and temperatures from about 250° to 300° F. In Friedel-Crafts type reactions, the reaction conditions are generally moderate, both as to temperature and pressure.

In the variation of the process shown in FIG. 2, the co-product stream containing dialkyl benzene and higher alkylated aromatic compounds is dealkylated to produce additional mono alkyl aromatic. This reaction can be considered the reverse reaction of the alkylation procedure and is generally conducted by subjecting the polyalkylated aromatic hydrocarbon with an active alkylation catalyst such as a Friedel-Crafts catalyst, at moderate temperatures in the presence of a large excess of an aromatic hydrocarbon such as benzene. It is also possible to subject the polyalkylated aromatic hydrocarbon to a silica-alumina catalyst at high temperature and lower pressure than would normally be used for alkylation with the same catalyst. This results in the formation of an alkene and a dealkylated product. Conditions such as temperature, pressure and relative amounts of components in such a dealkylation reaction are well known to those skilled in the art and need not be detailed here.

To more fully illustrate the present invention, the following, non-limiting examples are presented:

EXAMPLE 1

In this example, which is a comparative example showing the prior art process, excess benzene was alkylated with a $C_{10}$–$C_{13}$ chloro paraffin (RCl) mixture containing 90% secondary chloro paraffin and 10% primary chlorol paraffin. The alkylation reaction was conducted at a temperature of about 150°–180° F., at atmospheric pressure and utilized an aluminum chloride catalyst. The reactor charge had the following composition:

Benzene, g—4568
RCl, g—1898
AlCl$_3$, g—57

Following removal of benzene and free $C_{10}$–$C_{13}$ paraffin, there was produced the following reaction product:

Alkylate Product, g—1482
Recycle Alkylate, g
Diphenylalkane (DPA), g—172
Dialkylbenzene (DAB), g—137

After two acid washes, the alkylate product had a Sulfonate Klett Color of 33.

EXAMPLE 2

This example demonstrates the embodiment of the process shown in FIG. 1. The process of Example 1 was followed with the exception that the DPA stream was fractionated as in column 60, FIG. 1. The reactor charge has the following composition:

Benzene, g—4568
RCl, g—1898
AlCl$_3$, g—57
Recycle Alkylate, g—80

Following removal of benzene and free $C_{10}$–$C_{13}$ paraffin, there was produced the following reaction product:

Alkylate Product, g—1505
Recycle Alkylate, g—81
DPA—85
DAB—132

After two acid washes, the alkylate product had a Sulfonate Klett Color of 18.

EXAMPLE 3

In this example, the embodiment of the process illustrated in FIG. 2 is demonstrated. The procedure of Example 2 was followed with the exception that the DAB stream was dealkylated as in dialkylation reactor 66. The charge to the dealkylation reactor was as follows:

Benzene, g—4568
AlCl$_3$, g—57
DAB, g—205
HCl, g—2

The reaction product from the dealkylation reactor together witQ 69 g of recycle alkylate and 1898 g of RCl was then charged to an alkylation reactor such as reactor 16.

Following separation of benzene and free $C_{10}$–$C_{13}$ paraffin, there was produced the following reaction product:

Alkylate Product, g—1652
Recycle Alkylate, g—74
DPA, g—102
DAB, g—239

After two acid washes, the alkylate product had a Sulfonate Klett Color of 24.

As can be seen from comparing the results of Examples 1, 2 and 3, by conducting the prior art process wherein there is no recycle of alkylate, there is a smaller recovery of alkylate product with a loss of the desired mono alkyl benzene. In this regard, it is to be noted that the diphenylalkane stream contains mono alkyl benzene. Referring to Example 2, it can be seen that when the diphenylalkane stream containing the mono alkyl benzene is fractionated to recover the mono alkyl benzene (recycle alkylate), there is an increase in alkylate product. Moreover, and more importantly, there is a marked reduction in the amount of mono alkyl benzene lost from the system. In this regard, it is to be noted that the diphenylalkane containing the mono alkyl benzene is fractionated such that substantially all of the mono alkyl benzene is removed leaving only the lower value diphenylalkane product. With reference to Example 3, it can be seen that if, in addition to fractionating the diphenylalkane stream and recycling the mono alkyl benzene recovered therefrom, the dialkyl benzene stream is also dealkylated as in reactor 66, there is a dramatic increase in the amount of alkylate product recovered compared with the prior art process or even the improved process for fractionating the diphenylalkane stream and recycling the alkylate. Moreover, as in the case of the process of Example 2, there is virtually none of the mono alkyl benzene product lost to a lower value stream.

It can also be seen that the process of the present invention markedly improves color characteristics of the alkylate product. Note that in the prior art process (Example 1), two acid washings produce a product with a Sulfonate Klett Color of 33, whereas if the process as set forth in FIG. 1 is carried out (Example 2), the alkylate product has a Sulfonate Klett Color of 18 after two acid washings. By carrying out the process depicted in FIG. 2 (Example 3), the alkylate product has a Sulfonate Klett Color of 24. Thus, for the same number of acid washes, i.e. two, using the process of the present invention (Example 2 or 3), the color characteristics of the alkylate product are greatly enhanced as compared with the alkylate product obtained by the prior art process (Example 1). Conversely, it will be recognized that acceptable Sulfonate Klett Color can be obtained without the necessity for two acid washes. In fact, it has been found that alkylate product of acceptable color characteristics can be obtained with only a single acid washing if the process of the present invention is utilized in preparing the alkylate product. Thus, superior alkylate product can be obtained with the same number of acid washes used in the prior art process or, the product having essentially the same color characteristics of that obtained by the prior art process can be achieved with less acid washings.

The foregoing disclosure and description of the invention is illustrative and explanatory thereof, and various changes in the method steps may be made within the scope of the appended claims without departing from the spirit of the invention.

What is claimed is:

1. In a process for the production of a mono alkyl aromatic wherein a mono nuclear aromatic compound and an alkylating agent are subjected to an alkylation reaction to produce a reaction product comprising unreacted mono nuclear aromatic compound, alkanes, mono alkyl aromatic, dialkyl aromatic and by-products, said reaction product being treated to remove unreacted mono nuclear aromatic compound and paraffins, and produce a crude product stream containing mono alkyl aromatic, dialkyl aromatic and color forming by-products, and wherein the majority of said mono alkyl aromatic is separated from said crude product stream to produce a higher boiling fraction containing a minor amount of mono alkyl aromatic, dialkyl aromatic and said color forming by-products, the improvement comprising separating said higher boiling fraction into a recycle stream containing mono alkyl aromatic and at least some of said color forming by-product and a co-product stream substantially free of said mono alkyl aromatic, and introducing said recycle stream into said alkylation reaction.

2. The process of claim 1 wherein said mono nuclear aromatic compound comprises benzene.

3. The process of claim 1 wherein said alkylating agent contains from about 8 to about 17 carbon atoms.

4. The process of claim 1 wherein said alkylating agent comprises a halo alkane.

5. The process of claim 4 wherein said halo alkane comprises a chloro alkane containing from about 8 to about 17 carbon atoms.

6. The process of claim 1 including subjecting at least a part of said co-product stream to a dealkylation reaction in the presence of a catalyst and an excess of said mono nuclear aromatic to produce a dealkylate stream and introducing said dealkylate stream into said alkylation reaction.

7. The process of claim 6 wherein said mono nuclear aromatic comprises benzene.

8. The process of claim 6 wherein said dealkylation is carried out in the presence of an acid catalyst.

* * * * *